(12) United States Patent
Lee

(10) Patent No.: US 11,021,541 B2
(45) Date of Patent: Jun. 1, 2021

(54) METHOD OF INHIBITING THE GONADOTROPIN-RELEASING HORMONE (GNRH) RECEPTOR BY ADMINISTERING A GHR-106 MONOCLONAL ANTIBODY

(71) Applicant: Vancouver Biotech Ltd., Vancouver (CA)

(72) Inventor: Gregory Lee, Vancouver (CA)

(73) Assignee: Vancouver Biotech Ltd., Vancouver (CA)

(*) Notice: Subject to any disclaimer, the term of this patent is extended or adjusted under 35 U.S.C. 154(b) by 0 days.

(21) Appl. No.: 16/939,829

(22) Filed: Jul. 27, 2020

(65) Prior Publication Data

US 2020/0354462 A1     Nov. 12, 2020

Related U.S. Application Data

(63) Continuation of application No. PCT/CA2019/050147, filed on Feb. 5, 2019.

(60) Provisional application No. 62/627,052, filed on Feb. 6, 2018.

(51) Int. Cl.
    *C07K 16/28*        (2006.01)
    *A61P 15/08*        (2006.01)

(52) U.S. Cl.
    CPC .......... *C07K 16/2869* (2013.01); *A61P 15/08* (2018.01); *C07K 2317/24* (2013.01); *C07K 2317/30* (2013.01); *C07K 2317/76* (2013.01)

(58) Field of Classification Search
    CPC ............ C07K 16/2869; C07K 2317/24; C07K 2317/30; C07K 2317/73; C07K 2317/76; C07K 2317/92; C07K 2317/94; A61P 15/08; A61P 35/00; A61P 15/00; A61K 2039/505; A61K 2039/545
See application file for complete search history.

(56) References Cited

U.S. PATENT DOCUMENTS 8,163,283 B2    4/2012    Lee
8,361,793 B2    1/2013    Lee
9,273,138 B2    3/2016    Lee

FOREIGN PATENT DOCUMENTS

WO    2011/026242 A1    3/2011
WO    2014/016702 A2    1/2014
WO    2018/119519 A1    7/2018

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Shaqiri A, et al. (2018) Sci. Rep. 8:7521-7530. (doi: 10.1038/s41598-018-25298-8).*
Lee, G., Anti-GNRH Receptor Monoclonal Antibodies are Long Acting Analogs of GNHR. Open Access Journal of Gynecology, 2016 1(4), 000123, ISSN: 2474-9230.
Lee, G., GHR106 Monoclonal Antibody is Bioequivalent to GnRH Peptide Analogs. Global Journal of Reproductive Medicine, 2017, 1(1):001-002, ISSN: 2575-8594.
Nagy et al., Targeting of Cytotoxic Luteinizing Hormone-Releasing Hormone Analogs to Breast, Ovarian, Endometrial, and Prostate Caners. Biol. Reprod. 73(5):851-859 (2005).
Vidarsson et al., IgG subclasses and allotypes: from structure to effector functions. Front. Immunol., 2014, 5:520.
Van der Zee et al., Inhibition of complement activation by IgG4 antibodies. Clin. Exp. Immunol., 1986, 64(2):415-422.
Silva et al., The S228P Mutation Prevents in Vivo and in Vitro IgG4 Fab-arm Exchange as Demonstrated using a Combination of NOvel Quantitative Immunoassays and Physiological Matrix Preparation. JBC, 2015, 290(9):5462-5469.
Kuroda et al., Computer-aided antibody design. Protein Engineering, Design and Selection 25(10):507-522 (2012).
Lee, Humanized GHR106 Monoclonal Antibody is a Biosimilar GnRH Antagonist, Invest in Gynecol Res & Womens Health, Apr. 6, 2018, 1(5), ISSN: 2577-2015.

* cited by examiner

*Primary Examiner* — Robert S Landsman
(74) *Attorney, Agent, or Firm* — Oyen Wiggs Green & Mutala LLP

(57) ABSTRACT

An antibody-based GnRH receptor antagonist and methods of making and using same are disclosed. The antibody-based GnRH receptor antagonist is a GHR-106 monoclonal antibody (GHR-106) or an antigen-binding fragment thereof. GHR-106 or its IgG fragments can be utilized for therapeutic applications in the treatment of cancer and a range of sex hormone-related disorders or conditions in male or female subjects for which decapeptide GnRH antagonists are currently used.

17 Claims, 5 Drawing Sheets

Specification includes a Sequence Listing.

Amino Acid Sequence N1-30

- Mouse     MANNASLEQDPNHCSAINNSIPLIQGKLPT(SEQ ID NO:1)
- Monkey   MANSALPEQNQNHCSVINNSIPLMQGNLPT(SEQ ID NO:2)
- Human    MANSASPEQNQNHCSAINNSIPLMQGNLPT(SEQ ID NO:3)

Summary of Amino Acid Substitutions among Mouse, Monkey and Humans

- Mouse/Monkey: 8/30 amino acids
- Mouse/Human: 6/30 amino acids
- Monkey/Human: 2/30 amino acids (N6 L/S, N16 V/A: Neutral substitution)

FIG. 3

| Gene | GHR106 (10 or 20 µg/ml) | Antide (GnRH Antagonist) (0.1 µg/ml) |
|---|---|---|
| GnRH | ↑ | ↑ |
| GnRH receptor | NC | NC |
| $P_0$ | ↓ | ↓ |
| $P_1$ | ↑ | ↑ |
| $P_2$ | NC | NC |
| L37 | ↓ | ↓ |
| EGF | ↓ | ↓ |
| c-fos | NC | NC |
| P21 | ↑ | ↑ |
| Cyclin D1 | ↓ | ↓ |

FIG. 4

Construct: H7824

Name: pLEV123-Humanized GHR106-hIgG4(S228P)

BackBone: hIgG4-S228P

Insert sequence:

ATGGACCCCAAGGGCAGCCTGAGCTGGAGAATCCTGCTGTTCCTGAGCCTGGCCTTCGAGCTGAGCTACGGCCAG
GTTCAGTTGCAAGAGTCTGGTCCCGGCCTGGTTAAACCCTCTGAGACTTTGAGCTTGACATGCACCGTAAGCGGCT
TCTCTCTGAGCCGGTACTCTGTACACTGGATTCGACAGCCTCCTGGCAAGGGCCTGGAATGGATTGGCATGATCTG
GGGCGGCGGAAGTACAGATTATAACCCTTCCTTGAAGAGCCGCGTCACCATCTCTAAGGACAACAGCAAGTCCCA
GGTCTTCCTGAAGATGTCAAGCGTCACCGCTGCCGACACCGCCATGTACTACTGTGCACGGGGGAATGACGGATA
CTACAGTTTCGCATATTGGGGCCAGGGAACACTGGTTACAGTGTCTAGTGCTAGCACCAAGGGCCCCAGCGTGTTT
CCTCTCGCTCCCTGCAGCCGGAGCACATCCGAGAGCACCGCTGCTCTGGGCTGTCTCGTGAAGGACTACTTCCCTG
AACCCGTCACCGTCAGCTGGAATAGCGGCGCCCTGACATCCGGCGTCCACACATTCCCCGCTGTCCTGCAGAGCAG
CGGCCTGTACAGCCTGAGCTCCGTGGTCACCGTGCCTAGCAGCAGCCTGGGAACAAAGACCTACACCTGCAACGT
GGACCATAAGCCCTCCAACACCAAGGTGGACAAGCGGGTGGAATCCAAGTATGGACCCCCTGTCCTCCTTGCCCCT
GCTCCTGAATTTCTCGGAGGCCCCTCCGTCTTCCTGTTTCCCCCAAGCCCAAGGACACCCTGATGATCTCCCGGAC
ACCCGAAGTCACCTGCGTCGTGGTGGATGTCAGCCAGGAAGATCCCGAGGTGCAGTTCAACTGGTACGTGGACG
GAGTGGAGGTGCATAACGCCAAAACCAAGCCCAGGGAAGAGCAGTTCAACAGCACCTATCGGGTCGTGTCCGTG
CTCACCGTCCTGCATCAGGATTGGCTCAACGGCAAGGAGTACAAGTGCAAGGTGTCCAACAAGGGCCTGCCCTCC
TCCATCGAGAAGACCATCTCCAAGGCTAAGGGCCAACCTCGGGAGCCCCAAGTGTATACCCTCCCTCCAGCCAGG
AGGAGATGACCAAGAATCAAGTGAGCCTGACCTGCCTCGTGAAGGGATTTTACCCCTCCGACATCGCTGTGGAAT
GGGAAAGCAATGGCCAACCTGAGAACAACTACAAGACCACACCCCCCGTGCTGGACTCCGATGGCTCCTTCTTCCT
GTACAGCAGGCTGACCGTGGACAAATCCCGGTGGCAAGAGGGAAACGTGTTCAGCTGCTCCGTGATGCACGAGG
CTCTCCACAACCACTACACCCAGAAGAGCCTCTCCCTGAGCCTCGGCTAGTAA (SEQ ID NO:4)

Translation:

MDPKGSLSWRILLFLSLAFELSYGQVQLQESGPGLVKPSETLSLTCTVSGFSLSRYSVHWIRQPPGKGLEWIGMIWGGG
STDYNPSLKSRVTISKDNSKSQVFLKMSSVTAADTAMYYCARGNDGYYSFAYWGQGTLVTVSSASTKGPSVFPLAPCSR
STSESTAALGCLVKDYFPEPVTVSWNSGALTSGVHTFPAVLQSSGLYSLSSVVTVPSSSLGTKTYTCNVDHKPSNTKVDK
RVESKYGPPCPPCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCLVKGFYP
SDIAVEWESNGQPENNYKTTPPVLDSDGSFFLYSRLTVDKSRWQEGNVFSCSVMHEALHNHYTQKSLSLSLG\*\*
(SEQ ID NO:5)

FIG. 5

Construct: L7824

Name: pLEV123-Humanized GHR106-hKappa

BackBone: hKappa

Insert sequence:

ATGGAGACCGACACCCTGCTGCTCTGGGTGCTGCTGCTCTGGGTGCCCGGCTCCACCGGAGATATCGTAATGACTC
AGTCCCCCGATAGCCTCGCTGTGTCATTGGGTGAACGGGCAACTATTAACTGTAAGTCATCACAAAGCCTCCTTAA
TTCTAGGACCAGGAAAAACTACCTGGCATGGTATCAACAGAAGCCAGGACAGTCACCAAAGCTGCTGATCTACTG
GGCTTCTACAAGAGAGAGTGGAGTGCCAGACCGCTTCTCCGGCTCCGGGAGCGGCACTGATTTTACCCTCACTATC
AGCTCCCTTCAGGCAGAGGATGTGGCCGTGTACTATTGCAAGCAGAGCTACAACCTCTACACCTTCGGCCAGGGG
ACTAAACTGGAAATTAAGCGGACCGTGGCCGCCCCAGCGTGTTCATCTTCCCTCCCAGCGACGAGCAGCTGAAG
TCTGGCACCGCCAGCGTGGTGTGCCTGCTGAACAACTTCTACCCCCGCGAGGCCAAGGTGCAGTGGAAGGTGGAC
AACGCCCTGCAGAGCGGCAACAGCCAGGAGAGCGTGACCGAGCAGGACTCCAAGGACAGCACCTACAGCCTGAG
CAGCACCCTGACCCTGAGCAAGGCCGACTACGAGAAGCACAAGGTGTACGCCTGCGAGGTGACCCACCAGGGAC
TGTCTAGCCCCGTGACCAAGAGCTTCAACCGGGGCGAGTGCTAA (SEQ ID NO:6)

Translation:

METDTLLLWVLLLWVPGSTGDIVMTQSPDSLAVSLGERATINCKSSQSLLNSRTRKNYLAWYQQKPGQSPKLLIYWAST
RESGVPDRFSGSGSGTDFTLTISSLQAEDVAVYYCKQSYNLYTFGQGTKLEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLSSPVTKSFNRGEC*
(SEQ ID NO:7)

FIG. 6

SEQUENCE LISTING

```
<160> NUMBER OF SEQ ID NOS: 7

<210> SEQ ID NO 1
<211> LENGTH: 30
<212> TYPE: PRT
<213> ORGANISM: Mus musculus

<400> SEQUENCE: 1

Met Ala Asn Asn Ala Ser Leu Glu Gln Asp Pro Asn His Cys Ser Ala
1               5                   10                  15

Ile Asn Asn Ser Ile Pro Leu Ile Gln Gly Lys Leu Pro Thr
            20                  25                  30

<210> SEQ ID NO 2
<211> LENGTH: 30
<212> TYPE: PRT
<213> ORGANISM: Pan troglodytes

<400> SEQUENCE: 2

Met Ala Asn Ser Ala Leu Pro Glu Gln Asn Gln Asn His Cys Ser Val
1               5                   10                  15

Ile Asn Asn Ser Ile Pro Leu Met Gln Gly Asn Leu Pro Thr
            20                  25                  30

<210> SEQ ID NO 3
<211> LENGTH: 30
<212> TYPE: PRT
<213> ORGANISM: Homo sapiens

<400> SEQUENCE: 3

Met Ala Asn Ser Ala Ser Pro Glu Gln Asn Gln Asn His Cys Ser Ala
1               5                   10                  15

Ile Asn Asn Ser Ile Pro Leu Met Gln Gly Asn Leu Pro Thr
            20                  25                  30

<210> SEQ ID NO 4
```

<211> LENGTH: 1410
<212> TYPE: DNA
<213> ORGANISM: Artificial Sequence
<220> FEATURE:
<223> OTHER INFORMATION: Artificial Construct

<400> SEQUENCE: 4

```
atggacccca agggcagcct gagctggaga atcctgctgt tcctgagcct ggccttcgag      60
ctgagctacg gccaggttca gttgcaagag tctggtcccg gcctggttaa accctctgag     120
actttgagct tgacatgcac cgtaagcggc ttctctctga ccggtactc tgtacactgg      180
attcgacagc ctcctggcaa gggcctggaa tggattggca tgatctgggg cggcggaagt     240
acagattata acccttcctt gaagagccgc gtcaccatct ctaaggacaa cagcaagtcc     300
caggtcttcc tgaagatgtc aagcgtcacc gctgccgaca ccgccatgta ctactgtgca     360
cgggggaatg acggatacta cagtttcgca tattggggcc agggaacact ggttacagtg     420
tctagtgcta gcaccaaggg ccccagcgtg tttcctctcg ctcccctgca gccggagcaca     480
tccgagagca ccgctgctct gggctgtctc gtgaaggact acttccctga acccgtcacc     540
gtcagctgga atagcggcgc cctgacatcc ggcgtccaca cattccccgc tgtcctgcag     600
agcagcggcc tgtacagcct gagctccgtg gtcaccgtgc ctagcagcag cctgggaaca     660
aagacctaca cctgcaacgt ggaccataag ccctccaaca ccaaggtgga caagcgggtg     720
gaatccaagt atggaccccc ctgtcctcct tgccctgctc ctgaatttct cggaggcccc     780
tccgtcttcc tgtttccccc caagcccaag gacacactga tgatctcccg gacacccgaa     840
gtcacctgcg tcgtggtgga tgtcagccag gaagatcccg aggtgcagtt caactggtac     900
gtggacggag tggaggtgca taacgccaaa accaagccca gggaagagca gttcaacagc     960
acctatcggg tcgtgtccgt gctcaccgtc ctgcatcagg attggctcaa cggcaaggag    1020
tacaagtgca aggtgtccaa caagggcctg cctcctcca tcgagaagac catctccaag    1080
gctaagggcc aacctcggga gccccaagtg tataccctcc ctcccagcca ggaggagatg    1140
accaagaatc aagtgagcct gacctgcctc gtgaagggat tttaccctc cgacatcgct    1200
gtggaatggg aaagcaatgg ccaacctgag aacaactaca agaccacacc ccccgtgctg    1260
gactccgatg gctccttctt cctgtacagc aggctgaccg tggacaaatc ccggtggcaa    1320
gagggaaacg tgttcagctg ctccgtgatg cacgaggctc tccacaacca ctacacccag    1380
aagagcctct ccctgagcct cggctagtaa                                     1410
```

<210> SEQ ID NO 5
<211> LENGTH: 468
<212> TYPE: PRT
<213> ORGANISM: Artificial Sequence
<220> FEATURE:
<223> OTHER INFORMATION: Artificial Construct

<400> SEQUENCE: 5

```
Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Glu Ser Gly
            20                  25                  30

Pro Gly Leu Val Lys Pro Ser Glu Thr Leu Ser Leu Thr Cys Thr Val
        35                  40                  45

Ser Gly Phe Ser Leu Ser Arg Tyr Ser Val His Trp Ile Arg Gln Pro
    50                  55                  60

Pro Gly Lys Gly Leu Glu Trp Ile Gly Met Ile Trp Gly Gly Gly Ser
```

```
            65                  70                  75                  80
        Thr Asp Tyr Asn Pro Ser Leu Lys Ser Arg Val Thr Ile Ser Lys Asp
                        85                  90                  95

Asn Ser Lys Ser Gln Val Phe Leu Lys Met Ser Ser Val Thr Ala Ala
                       100                 105                 110

Asp Thr Ala Met Tyr Tyr Cys Ala Arg Gly Asn Asp Gly Tyr Tyr Ser
                       115                 120                 125

Phe Ala Tyr Trp Gly Gln Gly Thr Leu Val Thr Val Ser Ser Ala Ser
                       130                 135                 140

Thr Lys Gly Pro Ser Val Phe Pro Leu Ala Pro Cys Ser Arg Ser Thr
        145                 150                 155                 160

Ser Glu Ser Thr Ala Ala Leu Gly Cys Leu Val Lys Asp Tyr Phe Pro
                            165                 170                 175

Glu Pro Val Thr Val Ser Trp Asn Ser Gly Ala Leu Thr Ser Gly Val
                        180                 185                 190

His Thr Phe Pro Ala Val Leu Gln Ser Ser Gly Leu Tyr Ser Leu Ser
                        195                 200                 205

Ser Val Val Thr Val Pro Ser Ser Ser Leu Gly Thr Lys Thr Tyr Thr
                210                 215                 220

Cys Asn Val Asp His Lys Pro Ser Asn Thr Lys Val Asp Lys Arg Val
        225                 230                 235                 240

Glu Ser Lys Tyr Gly Pro Pro Cys Pro Pro Cys Pro Ala Pro Glu Phe
                        245                 250                 255

Leu Gly Gly Pro Ser Val Phe Leu Phe Pro Pro Lys Pro Lys Asp Thr
                        260                 265                 270

Leu Met Ile Ser Arg Thr Pro Glu Val Thr Cys Val Val Val Asp Val
                    275                 280                 285

Ser Gln Glu Asp Pro Glu Val Gln Phe Asn Trp Tyr Val Asp Gly Val
                        290                 295                 300

Glu Val His Asn Ala Lys Thr Lys Pro Arg Glu Glu Gln Phe Asn Ser
        305                 310                 315                 320

Thr Tyr Arg Val Val Ser Val Leu Thr Val Leu His Gln Asp Trp Leu
                            325                 330                 335

Asn Gly Lys Glu Tyr Lys Cys Lys Val Ser Asn Lys Gly Leu Pro Ser
                        340                 345                 350

Ser Ile Glu Lys Thr Ile Ser Lys Ala Lys Gly Gln Pro Arg Glu Pro
                        355                 360                 365

Gln Val Tyr Thr Leu Pro Pro Ser Gln Glu Glu Met Thr Lys Asn Gln
                370                 375                 380

Val Ser Leu Thr Cys Leu Val Lys Gly Phe Tyr Pro Ser Asp Ile Ala
        385                 390                 395                 400

Val Glu Trp Glu Ser Asn Gly Gln Pro Glu Asn Asn Tyr Lys Thr Thr
                            405                 410                 415

Pro Pro Val Leu Asp Ser Asp Gly Ser Phe Phe Leu Tyr Ser Arg Leu
                        420                 425                 430

Thr Val Asp Lys Ser Arg Trp Gln Glu Gly Asn Val Phe Ser Cys Ser
                        435                 440                 445

Val Met His Glu Ala Leu His Asn His Tyr Thr Gln Lys Ser Leu Ser
                    450                 455                 460

Leu Ser Leu Gly
        465

<210> SEQ ID NO 6
```

<211> LENGTH: 720
<212> TYPE: DNA
<213> ORGANISM: Artificial Sequence
<220> FEATURE:
<223> OTHER INFORMATION: Artificial Construct

<400> SEQUENCE: 6

```
atggagaccg acaccctgct gctctgggtg ctgctgctct gggtgcccgg ctccaccgga      60
gatatcgtaa tgactcagtc ccccgatagc ctcgctgtgt cattgggtga acgggcaact     120
attaactgta agtcatcaca aagcctcctt aattctagga ccaggaaaaa ctacctggca     180
tggtatcaac agaagccagg acagtcacca aagctgctga tctactgggc ttctacaaga     240
gagagtggag tgccagaccg cttctccggc tccggagcg gcactgattt taccctcact      300
atcagctccc ttcaggcaga ggatgtggcc gtgtactatt gcaagcagag ctacaacctc     360
tacaccttcg gccaggggac taaactggaa attaagcgga ccgtggccgc ccccagcgtg     420
ttcatcttcc ctcccagcga cgagcagctg aagtctggca ccgccagcgt ggtgtgcctg     480
ctgaacaact ctacccccg cgaggccaag gtgcagtgga aggtggacaa cgccctgcag      540
agcggcaaca gccaggagag cgtgaccgag caggactcca aggacagcac ctacagcctg     600
agcagcaccc tgaccctgag caaggccgac tacgagaagc acaaggtgta cgcctgcgag     660
gtgacccacc agggactgtc tagccccgtg accaagagct tcaaccgggg cgagtgctaa     720
```

<210> SEQ ID NO 7
<211> LENGTH: 239
<212> TYPE: PRT
<213> ORGANISM: Artificial Sequence
<220> FEATURE:
<223> OTHER INFORMATION: Artificial Construct

<400> SEQUENCE: 7

```
Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Lys Gln Ser Tyr Asn Leu Tyr Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
```

```
            195                 200                 205
Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

METHOD OF INHIBITING THE GONADOTROPIN-RELEASING HORMONE (GNRH) RECEPTOR BY ADMINISTERING A GHR-106 MONOCLONAL ANTIBODY

CROSS-REFERENCE TO RELATED APPLICATIONS

This application is a continuation of Patent Cooperation Treaty patent application No. PCT/CA2019/050147 filed 5 Feb. 2019, which claims the benefit of U.S. provisional patent application No. 62/627,052 filed 6 Feb. 2018. Both of the foregoing applications are incorporated by reference herein in their entireties.

REFERENCE TO A SEQUENCE LISTING

This application contains an ASCII text file Sequence Listing in computer readable form. The computer readable form filed herewith is incorporated by reference as part of this specification (file name V101_0021_Seq_List.txt, date recorded 20 Jul. 2020, size 11 KB).

TECHNICAL FIELD

Some embodiments of the present invention relate to the field of immunology and medicine, including medicine for the treatment of cancer and sex hormone-related health conditions or diseases. Some embodiments of the present invention relate to the field of monoclonal antibodies or antigen-binding fragments thereof that target the gonadotropin-releasing hormone (GnRH) receptor and act as GnRH antagonists and methods of making and using same.

BACKGROUND

Gonadotropin-releasing hormone (GnRH) is a decapeptide hormone that stimulates the release of gonadotropin, luteinizing hormone (LH) and follicle stimulating hormone (FSH) from the anterior pituitary through specific binding to the GnRH receptor. The GnRH receptor is located on the external membrane of many cell types and tissues, primarily in cancer cells, the anterior pituitary and reproductive organs or tissues. Although the function of the GnRH receptor in cancer cells is different from the function of the GnRH receptor in the anterior pituitary cells, the sequence and structure of the GnRH receptor is the same as between these different types of cells.

The administration of GnRH analogs that are antagonistic to the normal function of GnRH has been used for the treatment of a variety of sex hormone-related conditions or disorders such as reproductive diseases (in both males and females), infertility, assisted reproductive therapy such as in vitro fertilization (IVF) or egg donation (e.g. to control ovarian stimulation), contraception including inhibition of ovulation, medical transition for transgender people or sex reassignment therapy, whether male-to-female or female-to-male, and whether in conjunction with sex reassignment surgery or not, endometriosis, endometrial thinning, adenomyosis, endometrial hyperplasia, uterine leiomyoma (uterine fibroids), premenstrual syndrome, benign prostatic hypertropy, ovarian disorders, polycystic ovary disease, precocious puberty, and the like.

GnRH analogs have also been used in the treatment of some types of cancers including cancers of the prostate, breast and ovary, as well as cancers of the endometrium, cervix, placenta, pancreas, colon, lung, liver, kidney, or brain, or glioblastoma, lymphoma, leukemia, melanoma or neuroblastoma. It has been established that the GnRH is a pan cancer marker, being highly expressed on the cell surface of many different types of cancers, particularly at more advanced stages of such cancers (see e.g. U.S. Pat. No. 8,163,283, which is incorporated by reference herein in its entirety for all purposes). It has also been established that GnRH analogs (both agonists and antagonists) can induce apoptosis in cancer cells.

Examples of synthetic GnRH antagonists include, among others, antide, cetrorelix, abarelix, degarelix, ganirelix and elagolix.

Some synthetic GnRH analogs that are commonly used as GnRH antagonists are structurally modified decapeptide analogs of GnRH. The structures of some GnRH decapeptidic analogs substantially differ from that of GnRH where five of the ten amino acids are unnatural and of D-configuration. GnRH decapeptidic analogs that act as antagonists of GnRH compete directly with endogenous GnRH for binding to the GnRH receptor, with a rapid decrease in LH and FSH upon administration. GnRH decapeptidic analogs are thus known to produce immediate and direct effect. GnRH decapeptidic analogs are commonly used in clinical applications for treatment of fertility problems for at least this reason.

GnRH has a short half-life in human circulation of about 2-4 minutes. In general, GnRH decapeptide analogs have a short half-life in human circulation, for example ranging from approximately 3-63 hours. Therefore, GnRH decapeptide analogs are useful for treating conditions that require only short-term treatments. In order to effect a long-term treatment, daily administration of GnRH decapeptide analogs would be necessary.

GHR-106 is a monoclonal antibody that binds to the GnRH receptor. GHR-106 was originally generated in mice that were immunized against a synthetic oligopeptide corresponding to the epitope present in amino acid residues 1-29 in the extracellular domains of human GnRH receptor. The original murine mGHR-106 has been modified into humanized forms for administration in humans. The humanized GHR-106 monoclonal antibody (hGHR-106) has been shown to be bioequivalent to the murine monoclonal GHR-106 (mGHR-106). The murine mGHR-106 and humanized hGHR-106, including the amino acid sequence of their variable regions, have been disclosed in WO 2011/026242 and U.S. Pat. No. 9,273,138, which are hereby incorporated herein by reference for all purposes.

Prior U.S. Pat. Nos. 8,163,283, 8,361,793 and 9,273,138 to Lee, which are all incorporated by reference herein in their entireties for all purposes, are related to potential clinical applications of GHR-106 and its humanized forms in the treatment of human cancer and sex hormone-related conditions or disorders. Monoclonal antibodies have a relatively long half-life in human circulation, for example the half-life of monoclonal GHR-106 in circulation is estimated to be from about 5 days to about 22 days.

There remains a need for improved GnRH antagonists, and in particular, antibody-based GnRH antagonists, for use as an alternative to GnRH decapeptide analogs. There remains a need for improved GnRH antagonists suitable for use in the treatment of cancer and sex hormone-related conditions or disorders.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a method of using a GHR-106 monoclonal antibody or an antigen binding fragment thereof as an antibody-based GnRH antagonist to treat cancer or a sex hormone-related condition or disorder.

One aspect of the invention provides a method of treating cancer or a sex hormone-related condition or disorder in a subject by administering to the subject a therapeutically effective amount of a GHR-106 monoclonal antibody or an antigen binding fragment thereof as a GnRH antagonist. In some aspects, the subject is a human. In some aspects, the GHR-106 monoclonal antibody is a humanized GHR-106 monoclonal antibody. In some aspects, the antigen binding fragment of the GHR-106 monoclonal antibody is derived form a humanized GHR-106 monoclonal antibody.

In some aspects, the GHR-106 monoclonal antibody or antigen binding fragment thereof has effector functions, e.g. can activate antibody-dependent cellular cytotoxicity (ADCC) or complement-dependent cytotoxicity (CDC). In some such aspects, the GHR-106 monoclonal antibody or antigen binding fragment thereof has an IgG1, IgG2 or IgG3 subtype. In some aspects, the GHR-106 monoclonal antibody or antigen binding fragment thereof having effector functions is used to treat cancer. In some aspects, the cancer is one in which the GnRH receptor in cancer cells of that type is overexpressed relative to healthy cells of that type.

In some aspects, the GHR-106 monoclonal antibody or antigen binding fragment thereof does not activate effector functions, e.g. cannot activate antibody-dependent cellular cytotoxicity (ADCC) or complement-dependent cytotoxicity (CDC). In some aspects, the GHR-106 monoclonal antibody or antigen binding fragment thereof inhibits complement activation. In some aspects, the GHR-106 monoclonal antibody or antigen binding fragment thereof is an IgG4 subtype. In some aspects, the GHR-106 monoclonal antibody or antigen binding fragment thereof has an S228P or equivalent mutation in a heavy chain of the GHR-106 monoclonal antibody to inhibit IgG4 Fab-arm exchange.

In some aspects, the GHR-106 monoclonal antibody or antigen binding fragment thereof is used to treat a sex hormone-related condition or disorder. In some aspects, the sex hormone-related condition or disorder is a condition that is known to be treatable by the administration of known GnRH antagonists, e.g. decapeptide GnRH antagonists such as antide or cetrorelix. In some aspects, the GHR-106 monoclonal antibody or antigen binding fragment thereof is used to treat a condition or disorder in which a longer half-life in circulation of the active treatment agent is desirable. In some aspects, the GHR-106 monoclonal antibody or antigen binding fragment thereof is used to control ovulation.

In some aspects the antigen binding fragment of the GHR-106 monoclonal antibody is an IgG antibody fragment. In some aspects, the IgG antibody fragment is an F(ab')$_2$, Fab, scFab or scFv. In some aspects, the antigen binding fragment has a half-life in human circulation in the range of approximately 12 to 20 hours. In some aspects, the GHR-106 monoclonal antibody has a half-life in human circulation in the range of approximately 5 to 22 days.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 3 is a comparative analysis of the amino acid sequences of the extracellular domains of GnRH receptors from human, monkey and mouse species. The amino acid sequences at the amino acid positions 1-30 of the GnRH receptor's (GnRHR) N-terminal extracellular portions from each of the species are listed, showing the amino acid substitutions in bold. The number of amino acid substitutions within the amino acid sequences at the peptide positions 1-30 of the GnRHR N-terminal extracellular portions compared between the three species is also summarized.

FIG. 4 shows the effects on expression of certain genes involved in cell proliferation, protein synthesis and cell cycle regulation in response to treatments of OC-3-VGH cancer cells with GHR-106 or antide.

FIG. 5 shows the DNA and amino acid sequences of humanized GHR106-hIgG4 construct H7824.

FIG. 6 shows the DNA and amino acid sequences of humanized GHR106-hkappa construct L7824.

DESCRIPTION

Figure 1A:
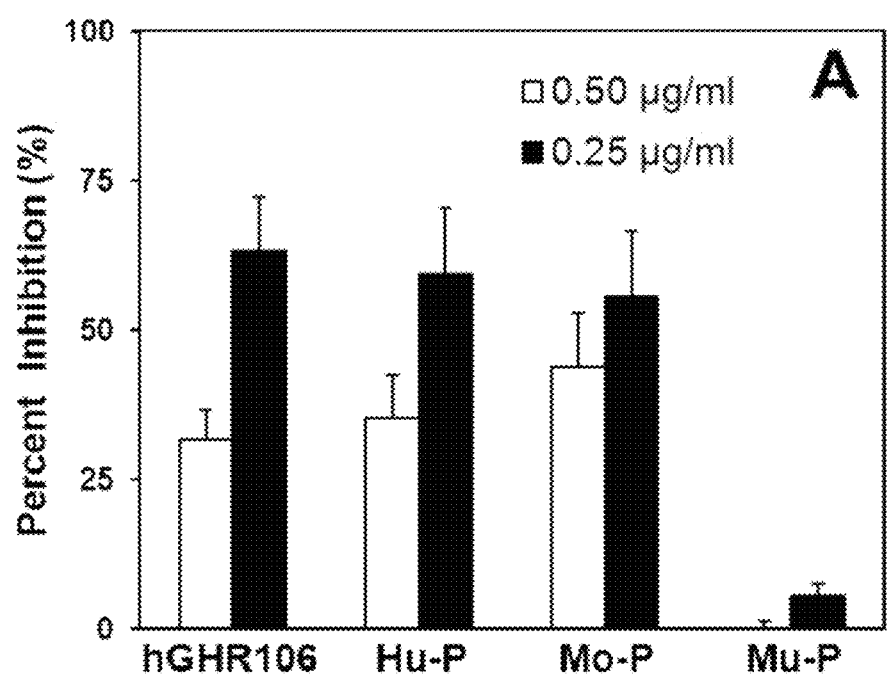
FIG. 1A shows competition of hGHR106 or N1-29 synthetic peptides of the extracellular domains of GnRH receptors from human (Hu-P), monkey (Mo-P) or mouse (Mu-P) with mGHR106 for binding to microwells coated with OC-3-VGH cancer cells. The white bars and black bars in FIG. 1A represent the different concentrations of mGHR106 (0.50 µg/ml and 0.25 µg/ml, respectively) used in each assay.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

As used herein, the term "GHR-106" encompasses a GHR-106 antibody derived from any species, and includes both murine GHR-106 (mGHR-106) and humanized GHR-106 (hGHR-106).

Some embodiments of the invention relate to the field of a GHR-106 antibody or an antigen-binding fragment thereof. GHR-106 binds to the extracellular domains of the human GnRH receptor, in particular, to the N-terminal amino acids at positions 1-29. The mGHR-106 or hGHR-106 antibody has an affinity for GnRH receptor with an affinity constant ($K_D$) of approximately 2-4 nM. GHR-106 competes with endogenous GnRH for binding to the GnRH receptor and is demonstrated in this disclosure to act as a GnRH antagonist.

Some embodiments of the invention relate to the discovery that the monoclonal antibody GHR-106 acts as a GnRH antagonist, similar in biological effect to GnRH decapeptide analogs that have been used as GnRH antagonists. Decapeptide GnRH antagonists such as antide and cetrorelix have been used for treatment of human cancer and sex hormone-related conditions or disorders, and based on the data in this specification, it can be soundly predicted that the GHR-106 antibody or an antigen binding fragment thereof that binds to the extracellular amino acids at the N-terminus of the GnRH receptor can similarly be used in the treatment of human cancer and sex hormone-related conditions or disorders. In some embodiments, mGHR-106 or hGHR-106 exhibits similar binding affinity and specificity towards a GnRH receptor as does a GnRH decapeptide analog that is an antagonist of GnRH.

In some embodiments, GHR-106 binds to the GnRH receptor expressed on the surface of a cancer cell to induce apoptosis and related cytotoxic killing of the cancer cell. In some embodiments, mGHR-106 and hGHR-106 exhibit similar effectiveness in their biological actions as GnRH decapeptide analogs that act as GnRH antagonists. This suggests that mGHR-106 and hGHR-106 are at least equally as effective, if not more effective, in targeting cancer cells as GnRH decapeptide analogs that act as antagonists of GnRH.

In some embodiments, GHR-106 exhibits identical or very similar molecular mechanisms of action as GnRH decapeptide analogs that are GnRH antagonists upon binding to a GnRH receptor. In some embodiments, hGHR-106 and GnRH decapeptide analogs that are GnRH antagonists exhibit identical to very similar gene regulation patterns upon their respective interaction with cancer cells. In some embodiments, the expression levels of the genes that are involved in proliferation or survival of cancer cells are substantially identical upon the respective interaction of hGHR-106 or a GnRH decapeptide analog with cancer cells. In an example embodiment, the GnRH decapeptide analog to which the hGHR-106 exhibits substantially identical biological effects upon interaction with cancer cells is antide.

Some aspects of the invention relate to the use of GHR-106 or an antigen-binding fragment thereof to treat cancer. In some embodiments, the fragment crystallizable region (Fc region) of the GHR-106 antibody is any one of an IgG1, IgG2 or IgG3 subtype. Based on the fact that these subtypes of IgG are known to activate processes such as complement-dependent cytotoxicity (CDC) or antibody-dependent cellular cytotoxicity (ADCC), it can be soundly predicted that GHR-106 antibodies of these subtypes will have utility in killing cancer cells. In some embodiments, a therapeutically effective mount of GHR-106, including hGHR-106, having an IgG1, IgG2 or IgG3 subtype is used clinically for cancer treatments in a mammal, including a human.

In some embodiments, the cancer treated by the GHR-106 antibody or antigen binding fragment thereof is a cancer in which the GnRH receptor is overexpressed in cancer cells of that type as compared to healthy cells of that type. In some embodiments, the level of expression or overexpression of the GnRH receptor in the cancer cells increases as the cancer advances through its various stages. In some embodiments, the cancer treated by the GHR-106 antibody or antigen binding fragment thereof is cancer of the prostate, breast, ovary, endometrium, cervix, placenta, pancreas, colon, lung, liver, kidney or brain, or is glioblastoma, lymphoma, leukemia, melanoma or neuroblastoma. See e.g. Nagy et al., *Biol. Reprod.* 73(5):851-859 (2005), which is incorporated by reference herein in its entirety for all purposes.

In some embodiments, the subtype of the GHR-106 antibody is selected to modulate the effector functions of the antibody. In some embodiments, the GHR-106 antibody or antigen binding fragment thereof is structurally modified to further modulate the effector functions of the antibody, for example by using an antigen binding fragment of the antibody that does not possess any effector functions. In some embodiments, the Fc region of the GHR-106 antibody is of the IgG4 subtype. In some embodiments, the GHR-106 antibody or antigen binding fragment thereof that does not possess any effector functions is used for the treatment of a sex hormone-related health condition or disorder. In some embodiments, the GHR-106 antibody having an IgG4 subtype is used for the treatment of sex hormone-related health conditions or disorders.

Without being bound by theory, it is believed that because the IgG4 antibody subtype does not activate complement-dependent cytotoxicity (CDC) or antibody-dependent cellular cytotoxicity (ADCC), use of the IgG4 antibody subtype for treatment of sex hormone-related health conditions or disorders, including fertility disorders, will minimize or eliminate the possibility of CDC and ADCC reactions upon the GHR-106 antibody binding to the anterior pituitary. See for example Vidarsson et al., *Front. Immunol.*, 2014, 5:520, which is incorporated by reference herein for all purposes.

Further, it has been demonstrated that IgG4 antibodies can actually inhibit complement activation (see e.g. van der Zee et al., *Clin. Exp. Immunol.*, 1986, 64(2):415-422, which is incorporated by reference herein for all purposes). Thus, in some embodiments, the GHR-106 monoclonal antibody or antigen binding fragment thereof is selected to inhibit complement activation. In some embodiments, the GHR-106 monoclonal antibody or antigen binding fragment thereof that inhibits complement activation is used to treat a sex hormone-related condition or disorder.

In some embodiments, the polynucleotide encoding the heavy chain of the hGHR-106 having an IgG4 subtype has a Fc region having a nucleotide sequent with at least 90% sequence identity to the sequence as set forth as SEQ ID NO:4 shown in FIG. 5, including any higher degree of similarity e.g. at least 91%, 92%, 93%, 94%, 95%, 96%, 97%, 97.5%, 98%, 98.5%, 99%, 99.5%, 99.7% or 99.9% sequence similarity. In some embodiments, the heavy chain of the hGHR-106 having an IgG4 subtype has an amino acid sequence having at least 90% sequence identity to the amino acid sequence set forth as SEQ ID NO:5 shown in FIG. 5, including any higher degree of similarity e.g. at least 91%, 92%, 93%, 94%, 95%, 96%, 97%, 97.5%, 98%, 98.5%, 99%, 99.5%, 99.7% or 99.9% sequence similarity.

In some embodiments, the polynucleotide encoding the light chain of the hGHR-106 antibody has a light chain nucleotide sequence having at least 90% sequence identity to the sequence as set forth in SEQ ID NO:6 shown in FIG. 6, including any higher degree of similarity e.g. at least 91%, 92%, 93%, 94%, 95%, 96%, 97%, 97.5%, 98%, 98.5%, 99%, 99.5%, 99.7% or 99.9% sequence similarity. In some embodiments, the light chain of the hGHR-106 having an IgG4 subtype has an amino acid sequence at least 90% sequence identity to the amino acid sequence set forth as SEQ ID NO:7 in FIG. 6, including any higher degree of similarity e.g. at least 91%, 92%, 93%, 94%, 95%, 96%, 97%, 97.5%, 98%, 98.5%, 99%, 99.5%, 99.7% or 99.9% sequence similarity.

In an example embodiment, a S228P or other similar mutation is engineered into the heavy chain of the IgG4 antibody. Without being bound by theory, it is believed that the S228P mutation or other equivalent mutation prevents the antibody from undergoing a recombinant process known as IgG4 Fab-arm exchange. Fab-arm exchange results in the formation of unwanted bispecific antibodies, which is known to have an undesirable effect on the specificity of the antibody to the target receptor. See, for example, Silva et al., *JBC*, 2015, 290(9):5462-5469, which is incorporated by reference herein for all purposes. An example embodiment of an IgG4 heavy chain having an S228P mutation is shown in FIG. 5 as SEQ ID NO:4 (nucleotide sequence) and SEQ ID NO:5 (amino acid sequence, note that S228 according to the EU numbering system is at position 250 in the amino acid SEQ ID NO:5).

Without being bound by theory, it is believed by the inventor that modification at the Fc region of the GHR-106 antibody to avoid activation of CDC and/or ADCC results in the elimination of unwanted effector functions of the antibody upon binding to GnRH receptor in the anterior pituitary. Some of the undesired effector functions include complement-dependent cytoxicity (CDC) and antibody-dependent cellular cytotoxicity (ADCC). These effector functions are useful in cancer treatment for killing cancer cells, but may not be desirable in fertility type or sex hormone-related treatments.

In some embodiments, the half-life of the GHR-106 antibody or antigen binding fragment thereof is adjusted by structurally modifying and/or reducing the size of the antibody. For example, in some embodiments, the antibody is provided as a F(ab')$_2$ fragment, which has a half-life in the range of about 12 to about 20 hours. In some embodiments, the antibody is provided as an Fab fragment, which has a half-life in the range of about 12 to about 20 hours. In some embodiments, the antibody is provided as an scFab fragment, which has a half-life in the range of at least about 12 hours. In some embodiments, the antibody is provided as an scFv fragment.

Provision of different antigen binding fragments of the GHR-106 antibody allows for the generation of a series of antibody-based GnRH antagonists for use as drugs with different half-lives for use in the clinical treatment of many fertility or sex hormone-related indications. Additionally, because decapeptide GnRH analogues are known to be able to induce apoptosis of cancer cells via their binding to the GnRH receptor, it can be predicted that such antibody fragments as F(ab')$_2$, Fab, scFab, ScFv or the like can also induce apoptosis of cancer cells via binding to the GnRH receptor, and therefore may be useful in the treatment of cancer.

In some embodiments, the GHR-106 antibody is provided as one or more active antigen binding fragments of GHR-106 for use in treating sex hormone-related health conditions or disorders. In some embodiments, the fragments are single chain fragments of the variable regions of GHR-106. In some embodiments, the fragments are fragments of GHR-106 of the IgG isotype. In some embodiments, the fragment is an F(ab')$_2$ fragment. In some embodiments, the F(ab')$_2$ fragment has a molecular weight of 110 KDa. In some embodiments, the fragment is a Fab fragment. In some embodiments, the Fab fragment has a molecular weight of 55 KDa. In some embodiments, the fragment is an scFab fragment. In some embodiments, the scFab fragment has a molecular weight of 25 KDa. In some embodiments, the fragment is an scFv fragment. In some embodiments, the scFv fragment has a molecular weight of 25 KDa. In some embodiments, combinations of different antigen binding fragments e.g. two or more of the fragments as described above, can be used as a drug for the treatment of cancer or a sex-hormone related condition or disorder.

In some embodiments, the circulation half-life of the GHR-106 antibody is approximately 5 to 21 days, including any value therebetween e.g. 6, 7, 8, 9, 10, 11, 12, 13, 14, 15, 17, 17, 18, 19 or 20 days, or 120 to 500 hours, including any value therebetween, e.g. 150, 175, 200, 225, 250, 275, 300, 325, 350, 375, 400, 425, 450, or 475 hours. By contrast, the circulation half life of cetrorelix is in a range of approximately 10 to 63 hours. GHR-106 has a much longer half life compared to the decapeptide GnRH antagonist cetrorelix, and therefore may require less frequent administration, which may improve patient compliance and/or the feasibility of a proposed treatment regime.

In some embodiments, the IgG antigen-binding fragments that are derived from GHR106, e.g. F(ab')$_2$, Fab, ScFab or ScFv, each has a circulation half-life of approximately 12 to 20 hours, including any value therebetween e.g. 13, 14, 15, 16, 17, 18 or 19 hours. The antigen-binding fragments of mGHR-106 or hGHR-106 have a shorter half-life compared to the mGHR-106 or hGHR106 antibodies. In some embodiments, protein engineering is used to provide GHR-106 antibodies or antigen binding fragments thereof that have a half-life within a desired range.

In some embodiments, the binding affinity and/or specificity of the GHR-106 monoclonal antibodies or antigen-binding fragments thereof are engineered using any suitable method to provide them with desired properties, e.g. a desired modified level of binding affinity and/or specificity. For example, antibodies can be engineered by using artificial systems such as synthetic antibody libraries or by using computational methods or protein design methodologies to alter the binding affinity and/or specificity of the GHR-106 monoclonal antibody or antigen binding fragment thereof. See e.g. Kuroda et al., *Protein Engineering, Design and Selection* 25(10):507-522 (2012), which is incorporated by reference herein in its entirety for all purposes. In some embodiments, one or more of the complementarity-determining regions (CDRs) of the GHR-106 antibodies or antigen binding fragments thereof are modified using such methods to modify their binding properties.

The monoclonal antibodies or antigen-binding fragments thereof described herein can be produced in any suitable manner, for example via recombinant production and expression in suitable host cells, including microbial host cells, mammalian cells, plant cells or insect cells.

The GHR-106 antibodies or antigen binding fragments thereof described herein can be formulated in any suitable manner for administration as a medicament. Thus, they can be combined with pharmaceutically acceptable excipients or other pharmaceutically suitable compounds to provide pharmaceutical compositions useful for the treatment of cancer or sex hormone-related health conditions or disorders.

In some embodiments, the GHR-106 antibodies or antigen binding fragments thereof described herein are administered in a therapeutically effective amount to a mammal, including a human, for the treatment of cancer. In some embodiments, the cancer is cancer of the prostate, breast, ovary, endometrium, cervix, placenta, pancreas, colon, lung, liver, kidney or brain. In some embodiments, the cancer is glioblastoma, lymphoma, leukemia, melanoma or neuroblastoma. In some embodiments, the cancer is one in which the GnRH receptor is overexpressed relative to healthy cells. In some embodiments, the GHR-106 antibody or antigen binding fragment thereof is derived from hGHR-106.

In some embodiments, the GHR-106 antibodies or antigen binding fragments thereof that are administered for the treatment of cancer possess effector functions. An antibody that possesses effector functions can activate, for example, complement-dependent cytoxicity (CDC) and/or antibody-dependent cellular cytotoxicity (ADCC) to enhance the killing of cancer cells. In some embodiments, the GHR-106 antibodies or antigen binding fragments thereof that possess effector functions have an IgG1, IgG2 or IgG3 isotype.

In some embodiments, the GHR-106 antibodies or antigen binding fragments thereof are administered in a therapeutically effective amount for the treatment of sex hormone-related health conditions or disorders in a mammal, including a human. The human may be a male or a female. In some embodiments, the sex hormone-related health condition or disorder is a reproductive disease (in a male or female subject), medical transition for transgender people including male-to-female (MTF) or female-to-male (FTM) sex reassignment therapy, whether or not accompanied by sex reassignment surgery, in vitro fertilization (IVF) or egg donation (e.g. to control ovarian stimulation), contraception including inhibition of ovulation, endometriosis, endometrial thinning, adenomyosis, endometrial hyperplasia, uterine leiomyoma (uterine fibroids), premenstrual syndrome, benign prostatic hypertropy, ovarian disorders, polycystic ovary disease, precocious puberty, and the like, and some types of cancers including cancers of the prostate, breast and ovary.

In some embodiments, the GHR-106 antibodies or antigen binding fragments thereof act as GnRH antagonists in the treatment of any condition that can be treated by known GnRH antagonists including antide or cetrorelix. In some embodiments, the GHR-106 antibodies or antigen binding fragments thereof are used in the treatment of a condition in which a longer half-life than that of known GnRH antagonists, including antide or cetrorelix, is desirable.

In some embodiments, the GHR-106 antibodies or antigen binding fragments thereof that are administered for the treatment of sex hormone-related health conditions or disorders do not possess effector functions. An antibody that does not possess effector functions cannot activate, for example, complement-dependent cytoxicity (CDC) or antibody-dependent cellular cytotoxicity (ADCC) pathways. In some embodiments, the GHR-106 antibodies or antigen binding fragments thereof that do not possess effector functions have an IgG4 subtype. In some embodiments, the GHR-106 antibodies or antigen binding fragments thereof inhibit complement activation. In some embodiments, the heavy chain of the antibody having the IgG4 subtype has a S228P mutation or an equivalent mutation, to prevent Fab-arm exchange. In some embodiments, the GHR-106 antibodies or antigen binding fragments thereof that do not possess effector functions are IgG antigen-binding fragments of GHR-106 antibodies. In some embodiments, the antigen binding fragments that do not possess effector functions are F(ab')$_2$, Fab, scFab or scFv IgG fragments of GHR-106 antibodies. In some embodiments, the GHR-106 antibodies or antigen binding fragments thereof are derived from hGHR-106.

In some embodiments, the GHR-106 antibodies or antigen binding fragments thereof are administered at dosage levels of 0.01-20 mg/kg to a human subject, or in amounts in the range of 0.01-5 mg/kg, or any intermediate value within those ranges, e.g. 0.05, 0.10, 0.15, 0.20, 0.50, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5 or mg/kg. The appropriate dosage to achieve a desired therapeutic effect may be selected by one skilled in the art, and may be higher or lower than the stated ranges. In some embodiments in which the binding affinity and/or specificity of the GHR-106 antibody or antigen binding fragment thereof has been modified, the dosage level of the modified antibody or antigen binding fragment thereof is modified appropriately.

In some embodiments, the GHR-106 antibodies or antigen binding fragments thereof are administered at repeated spaced apart intervals, for example every 5-30 days or any value therebetween, e.g. every 6, 7, 8, 9, 10, 11, 12, 13, 14, 15, 16, 17, 18, 19, 20, 21, 22, 23, 24, 25, 26, 27, 28 or 29 days; every 2-8 weeks or any value therebetween, e.g. every 3, 4, 5, 6 or 7 weeks, or every 2-6 months or any value therebetween, e.g. every 3, 4 or 5 months. In some embodiments, the GHR-106 antibodies or antigen binding fragments thereof that are administered to a human are humanized GHR-106 antibodies or antigen binding fragments thereof.

A typical route of administration of pharmaceutical compositions comprising antibodies is via injection, typically intravenous. However, any suitable mode of administration can be used in various embodiments.

EXAMPLES

Embodiments of the invention are further described with reference to the following examples, which are illustrative and not limiting in nature.

Example 1.0—Competitive Binding Assays

Figure 1B:
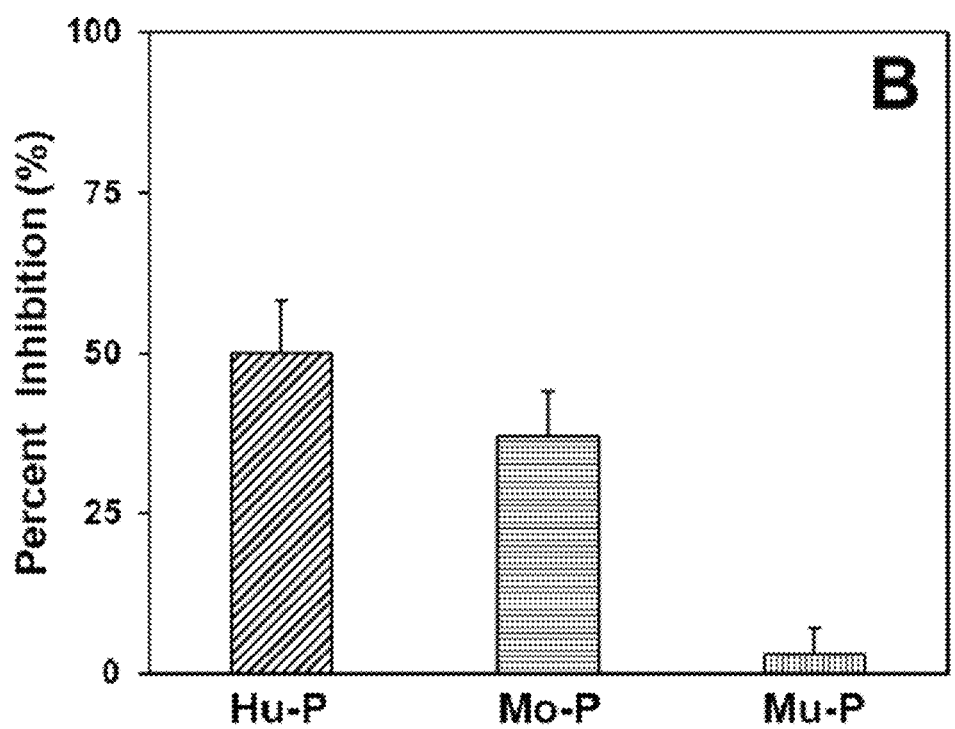
FIG. 1B shows competition of Hu-P, Mo-P or Mu-P with hGHR106 for binding to microwells coated with OC-3-VGH cancer cells.

Competitive binding assays were carried out according to accepted protocols, e.g. as described in U.S. Pat. No. 8,361,793. In FIG. 1A, microwells coated with OC-3-VGH cancer cells were used to compare the binding specificity between mGHR-106 and hGHR-106, as well as between mGHR-106 and N1-29 oligopeptides derived separately from human (Hu-P), monkey (Mo-P) and mouse (Mu-P) GnRH receptor. The N1-29 oligopeptides are derived from the N-terminal extracellular domains of GnRH receptors from each species. The amino acid sequence of each of Hu-P, Mo-P and Mu-P are shown as SEQ ID NO:1, SEQ ID NO:2 and SEQ ID NO:3 respectively in FIG. 3. In FIG. 1B, microwells coated with OC-3-VGH cancer cells were used to compare the binding specificity between hGHR-106 and each of Hu-P, Mo-P and Mu-P peptides.

With reference to FIG. 1A, percent inhibition of mGHR106 antibody binding to microwells coated with OC-3-VGH cancer cells by hGHR106 antibody, Hu-P, Mo-P and Mu-P peptides are shown. The white bars and black bars in FIG. 1A represent the different concentrations of mGHR106 (0.50 µg/ml and 0.25 µg/ml, respectively) used in each assay. With reference to FIG. 1B, percent inhibition of hGHR106 antibody binding to microwells coated with OC-3-VGH cancer cells by Hu-P, Mo-P and Mu-P (each at 1 µg/mL) are shown. Goat anti-human IgG-ALP (alkaline phosphatase labeled) was used as the probe, with error bars for duplicate assays indicated.

As shown in FIGS. 1A and 1B, mGHR106 and hGHR106 are mutually competitive in binding to GnRH receptors expressed on the surface of cultured cancer cells (OC-3-

VGH) as well as to the synthetic peptides. The N1-29 synthetic peptides of the extracellular domains of GnRH receptors from humans and monkey were also found to compete with the binding of mGHR106 and hGHR106 to human GnRH receptors expressed on the surface of cultured cancer cells but not with the synthetic peptide derived from mouse. Without being bound by theory, it is believed that such differential binding can be explained by the fact that a high degree of sequence homology was observed between the human and monkey N1-29 peptides (homology 94%), but not the between human and mouse N1-29 peptides (homology 79%) as shown in FIG. 3.

Example 2.0—Induction of Apoptosis of Cancer Cells

In order to compare the anti-proliferative effects (or apoptosis) between mGHR106 or hGHR106 and antide on cancer cells, In Situ Cell Death Detection Kit, POD (Roche, Canada) was employed for detection and quantitation of apoptosis of cultured and treated cancer cells in vitro. Briefly cancer cells were cultured in RPMI-1640 medium at 37° C. in a $CO_2$ (5%) incubator for 24 and/or 48 hours until all cancer cells are attached to microwells. Following removal of cell culture medium, fresh serum-free medium was added for an additional 3 hours incubation in a $CO_2$ incubator.

After the serum-free starvation period, the cells were incubated in fresh medium containing 10% fetal calf serum, and hGHR106, mGHR106 or antide of known concentration was added for co-incubation of 24 to 72 hours. As the negative control, normal mouse IgG or normal human IgG of the same concentration was used for the same incubation period.

At the end of incubation, the attached cells were removed from tissue culture wells by appropriate cell detachment solution. Apoptosis of treated cancer cells was quantitatively determined by TUNEL assay with the instructions provided by Cell Death Detection Kit, POD (Roche, Canada). Percent increases of cells with apoptosis after treatments with any one of hGHR106, mGHR106 and antide were obtained by subtracting spontaneous apoptosis from the negative control.

Figure 2A:
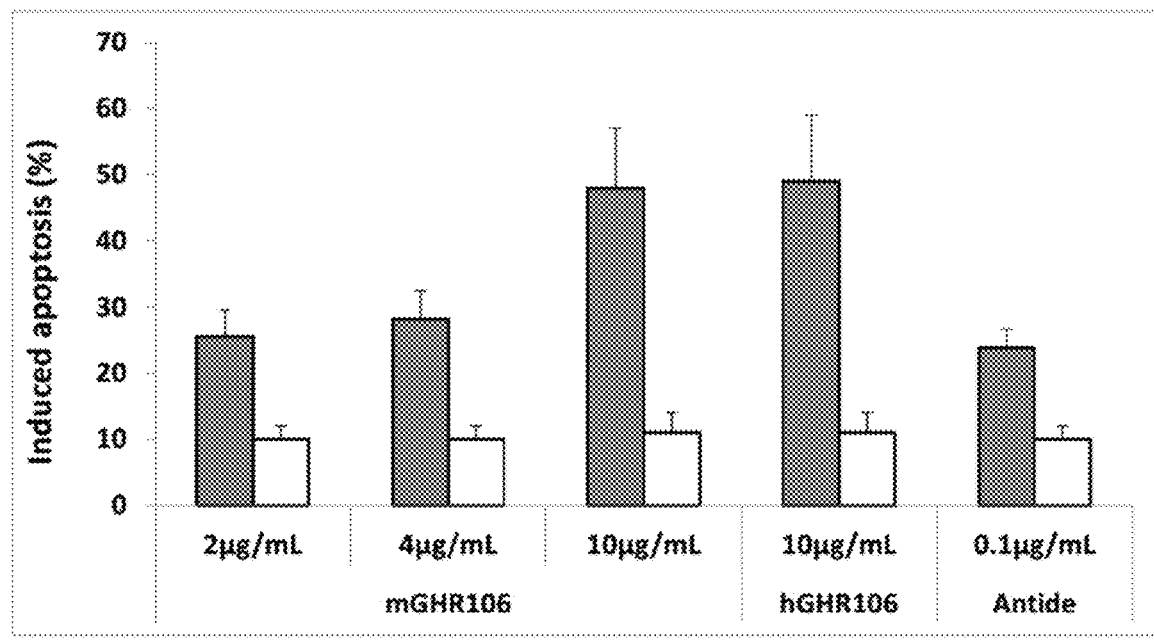
FIG. 2A shows percent increases in apoptosis of cancer cells in response to treatments of OC-3-VGH cancer cells with mGHR-106, hGHR-106 or antide.
Figure 2B:
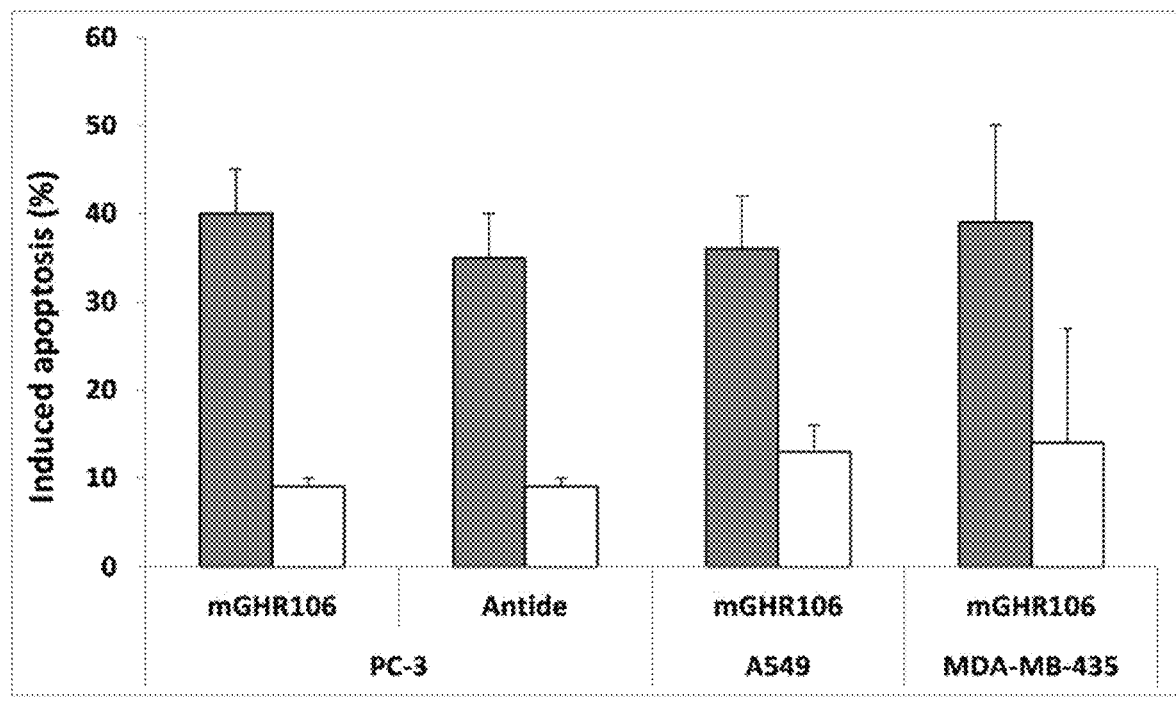
FIG. 2B shows percent increases in apoptosis of cancer cells in response to treatment of PC-3 prostate cancer cells, A549 lung cancer cells, and MDA-MB-435 breast cancer cells with mGHR-106, and to treatment of PC-3 prostate cancer cells with antide. Black bars show the assay results; white bars show the results for the negative control.

FIGS. 2A and 2B show the results of the comparative TUNEL apoptosis assays. The black bars in FIGS. 2A and 2B represent the percent increase of cells with apoptosis after treatment with mGHR-106, hGHR-106 or antide. The white bars represent the negative control, which was either 10 µg/mL normal mouse IgG or 10 µg/mL human IgG for each corresponding set of experiments. All results presented were statistically significant, with $p<0.01$ or $p<0.001$.

With reference to FIGS. 2A and 2B, mGHR-106 or hGHR-106 and antide exhibit very similar degrees of induced apoptosis on a molar basis (the molecular weights of GHR-106 and antide are 80 kDa and 1.5 kDa respectively). These results demonstrate that mGHR-106 or hGHR-106 acts similarly to the known GnRH antagonist antide in terms of their functional properties.

Example 3.0—Comparative Gene Regulation Studies

Comparative gene regulation upon administration of hGHR106 or the decapeptide GnRH analog antide was examined using conventional protocols, e.g. as described in U.S. Pat. No. 8,361,793. FIG. 4 shows a comparison of the gene regulation patterns of hGHR-106 and antide upon binding to human GnRH receptor on cancer cells. Expressions of a number of selected genes involved in the proliferation or survival of cancer cells were compared. The selected genes include: GnRH, GnRHR, $P_0$, $P_1$, $P_2$, L37, and EGF, c-fos, P21 and cyclin D1. $P_0$, $P_1$, $P_2$, and L37 are ribosomal proteins.

With reference to FIG. 4, expression of the examined genes was found to change significantly following the binding of either hGHR-106 or antide. Upon respective ligand treatments, hGHR-106 and antide were found to up-regulate GnRH expression 50%), while the expression of the GnRH receptor (GnRHR) remained unchanged. EGF (epidermal growth factor) and Cyclin D1 (cell cycle regulator) were both downregulated upon treatment of cancer cells with either ligand. As shown in FIG. 4, hGHR-106 and antide were found to have identical gene regulation pattern changes for the listed genes upon binding to GnRH receptor on cancer cells.

The results of this comparative gene regulation study demonstrates that hGHR-106 acts similarly to the exemplary GnRH decapeptide antagonist, antide. These results also support that the two ligands have similar molecular mechanisms of action, i.e. as GnRH antagonists, upon interaction with cancer cells.

Example 4.0—Comparison of Half-Lives

Table 1 is a comparison of the estimated half-lives of hGHR-106 and its IgG fragments, as well as selected GnRH decapeptide analogs, and clinically used human antibody drugs.

TABLE 1

Comparison of the estimated circulation half-life of hGHR106 and its IgG fragments, GnRH decapeptide analogs, and clinically used monoclonal antibodies

| Drug Candidates | Molecular species (Molecular Weight) | Estimated Half Life |
|---|---|---|
| GHR106 | IgG4 (humanized) (160 KDa) | 5-21 days |
| Anti-GnRH Receptor Mab (IgG4) | (Fab')$_3$ (110 KDa) | 12-20 hours |
|  | Fab (55 KDa) | 12-20 hours |
|  | ScFab (25 KDa) | ≤12 hours |
| Trastuzumab | Humanized (160 Kda) | 24.2 hours |
| Beracizumab | Humanized (160 Kda) | 480 hours |
| Panitumumab | Human (160 Kda) | 180 hours |
| GnRH decapeptide Analogs | Cetrorelix(Antagonist) (1.5 KDa) | 10-63 hours |
|  | Luprorelin(Agonist) (1.5 KDa) | 3 hours |
|  | Native GnRH (1.5 KDa) | 2-4 min |

As shown in Table 1, the series of different antibody-based fragments that act as GnRH antagonists have been shown to exhibit a range of different circulation half-lives. The inventor has hypothesized that the hGHR-106 antibody may be particularly useful in the treatment of cancer since hGHR-106 has a longer circulation half-life and stimulates effector functions such as CDC and ADCC reactions upon the ligand binding to the anterior pituitary. By contrast, the moderated half-life of the IgG fragments of hGHR-106 may have particular application in short-term treatments such as for the treatment of various sex hormone-related conditions, including fertility-related conditions. An example of such is ovulation inhibition to block LH/FSH release in the anterior pituitary.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

Without limitation, such aspects include the following:

A first aspect comprising a gonadotropin releasing hormone (GnRH) receptor antagonist comprising a GHR-106 monoclonal antibody or an antigen-binding fragment thereof.

A second aspect comprising the antagonist of the first aspect, wherein the fragment crystallizable region (Fc) of the GHR-106 antibody comprises any one of an IgG1, IgG2 or IgG3 subtype.

A third aspect comprising the antagonist of the first aspect, wherein the Fc region of the GHR-106 antibody comprises an IgG4 subtype.

A fourth aspect comprising the antagonist of the first aspect, wherein the antigen binding fragment of the GHR-106 antibody is one of an IgG F(ab')$_2$, a Fab, a scFab, or an scFv fragment.

A fifth aspect comprising the antagonist of the first aspect, wherein the GHR-106 antibody comprises a humanized GHR-106 antibody having a heavy chain having an amino acid sequence that has at least 90% sequence identity to the amino acid sequence of SEQ ID N0:5.

A sixth aspect comprising the antagonist of the fifth aspect, wherein the humanized GHR-106 antibody has light chain having an amino acid sequence that has at least 90% sequence identity to the amino acid sequence of SEQ ID NO:7.

A seventh aspect comprising the antagonist of the third aspect, wherein the fragment crystallizable (Fc) region of a heavy chain of the IgG4 antibody comprises a mutation from S to P at position 228 (according to the EU numbering convention for antibodies) or an equivalent mutation that inhibits Fab-arm exchange.

An eighth aspect comprising the antagonist of the first aspect, wherein one or more of the CDR regions of the GHR-106 monoclonal antibody or an antigen-binding fragment thereof are engineered to modify the binding affinity and/or specificity thereof.

A ninth aspect comprising the use of a GHR-106 monoclonal antibody or antigen binding fragment thereof as defined in any one of the preceding aspects in the use as defined in any one of the appended claims.

A tenth aspect comprising a method of administering to a subject a therapeutically effective amount of a GHR-106 monoclonal antibody or antigen binding fragment thereof as defined in any one of the preceding aspects to carry out a use as defined in any one of the appended claims.

---

The invention claimed is:

1. A method of inhibiting the gonadotropin-releasing hormone (GnRH) receptor in a subject, comprising administering to the subject a GHR-106 monoclonal antibody or an antigen-binding fragment thereof as a GnRH antagonist, wherein the GHR-106 monoclonal antibody or antigen-binding fragment thereof does not possess effector functions.

2. The method as defined in claim 1, wherein the GHR-106 antibody acts similarly to known decapeptide GnRH antagonists.

3. The method as defined in claim 2, wherein the known decapeptide GnRH antagonist is antide or cetrorelix.

4. The method as defined in claim 1, wherein the GHR-106 monoclonal antibody or antigen-binding fragment thereof inhibits complement activation.

5. The method as defined in claim 1, wherein the GHR-106 monoclonal antibody or antigen-binding fragment thereof comprises an IgG4 subtype.

6. The method as defined in claim 5, wherein the GHR-106 monoclonal antibody or antigen-binding fragment thereof comprises an S228P mutation in a heavy chain of the GHR-106 monoclonal antibody to inhibit IgG4 Fab-arm exchange.

7. The method as defined in claim 1, wherein the GHR-106 monoclonal antibody or antigen-binding fragment thereof is a GHR-106 monoclonal antibody.

8. The method as defined in claim 1, wherein the subject is female.

9. The method as defined in claim 1, wherein ovulation in the subject is controlled by the GHR-106 monoclonal antibody or antigen-binding fragment thereof.

10. The method as defined in claim 1, wherein the antigen-binding fragment of the GHR-106 monoclonal antibody comprises an IgG antibody fragment.

11. The method as defined in claim 10, wherein the IgG antibody fragment comprises an F(ab')2, Fab, scFab or scFv.

12. The method as defined in claim 1, wherein the subject is a human, and wherein the GHR-106 monoclonal antibody or antigen-binding fragment thereof comprises a humanized GHR-106 monoclonal antibody or antigen binding fragment thereof.

13. The method as defined in claim 1, wherein the GHR-106 monoclonal antibody or antigen-binding fragment thereof has a half-life in human circulation of between 5 and 22 days.

14. The method as defined in claim 1, wherein the GHR-106 antibody comprises a humanized GHR-106 antibody having a heavy chain having an amino acid sequence that has (a) at least 90% sequence identity to the amino acid sequence of SEQ ID NO:5 and (b) all three wild-type CDRs; and/or wherein the humanized GHR-106 antibody has light chain having an amino acid sequence that has (a) at least 90% sequence identity to the amino acid sequence of SEQ ID NO:7 and (b) all three wild-type CDRs.

15. The method as defined in claim 1, wherein the subject is a mammalian subject.

16. The method as defined in claim 15, wherein the subject is a human or a monkey.

17. The method as defined in claim 1, wherein the subject is male.

* * * * *